United States Patent [19]

Moeller

[11] Patent Number: 4,745,200

[45] Date of Patent: May 17, 1988

[54] METHOD OF PRODUCING SALTS OF 1,3-DIOXOLANE-4-CARBOXYLIC ACIDS AND METHOD OF USING SAME

[75] Inventor: Hinrich Moeller, Monheim, Fed. Rep. of Germany

[73] Assignee: Henkel Kommanditgesellschaft auf Aktien, Duesseldorf, Fed. Rep. of Germany

[21] Appl. No.: 808,594

[22] Filed: Dec. 13, 1985

[30] Foreign Application Priority Data

Dec. 29, 1984 [DE] Fed. Rep. of Germany ....... 3447783

[51] Int. Cl.$^4$ .............................................. C07D 317/00
[52] U.S. Cl. .................................... 549/450; 549/453; 424/70
[58] Field of Search ................................ 549/450, 453

[56] References Cited

U.S. PATENT DOCUMENTS 3,595,909  7/1971  Sheldon ............................ 260/528
3,657,277  4/1972  Ryrfors ............................ 549/453
3,896,115  7/1975  Wat .................................. 549/453

FOREIGN PATENT DOCUMENTS 2404072  8/1975  Fed. Rep. of Germany .
2903388  9/1979  Fed. Rep. of Germany .

OTHER PUBLICATIONS

Chemische Berichte 109, No. 11, 1976, pp. 3707-3727.
Angewandte Chemie, 69, No. 18/19 1957, pp. 600-608.

*Primary Examiner*—Nicky Chan
*Attorney, Agent, or Firm*—Ernest G. Szoke; Henry E. Millson, Jr.

[57] ABSTRACT

A new process for the production of salts of 1,3-dioxolane-4-carboxylic acid corresponding to the following formula

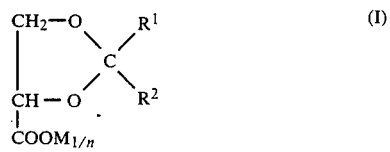

using as a starting material an isomer mixture of a 4-hydroxymethyl-1,3-dioxolane and a 5-hydroxy-1,3-dioxane obtained by reacting glycerin with an aldehyde or ketone having the formula $R^1R^2CO$. The 4-hydroxymethyl-1,3-dioxolane may be selectively oxidized from the isomer mixture in the presence of a platinum metal catalyst at an alkaline pH. The unreacted 5-hydroxy-1,3-dioxane may be extracted from the reaction mixture and the 1,3-dioxolane-4-carboxylic acid salt isolated in pure form.

8 Claims, No Drawings

METHOD OF PRODUCING SALTS OF 1,3-DIOXOLANE-4-CARBOXYLIC ACIDS AND METHOD OF USING SAME

BACKGROUND OF THE INVENTION

1. Field of the Invention

This invention relates to a new process for the production of salts of 1,3-dioxolane-4-carboxylic acids and to the use of these products as technical and, in particular, as cosmetic humectants.

2. Description of Related Art 1,3-dioxolane-4-carboxylic acids are suitable for use as starting materials for the production of glyceric acid and glyceric acid esters. Because they are not readily available, however, they have hitherto been obtained by acetalization or ketalization of glyceric acid esters. Glyceric acid may be obtained by direct oxidation of glycerin with nitric acid, although the process involved is complicated and gives poor yields.

The acetalization of glycerin with lower aldehydes and the ketalization of glycerin with lower ketones gives a mixture of isomeric cyclic acetals comprising 4-hydroxymethyl-1,3-dioxolanes and 5-hydroxy-1,3-dioxanes which are difficult to separate from one another on account of their similar boiling points (cf. J. Am. Chem. Soc. Vol. 50,(1928), pages 2242–2249 and 3120–3127).

Whereas 5-hydroxy-1,3-dioxane is formed in only small quantities in the formation of cyclic ketals, it is formed in quantities of up to 40% by weight of the isomer mixture in the reaction of glycerin with aldehydes, such as for example formaldehyde and acetaldehyde. The concentration of the 5-hydroxy-1,3-dioxane may continue to increase through gradual spontaneous rearrangement of the 4-hydroxymethyl-1,3-dioxolane, particularly if traces of acid are present. Accordingly, commercial glycerin formal may contain up to 80% by weight of 5-hydroxy-1,3-dioxane.

DESCRIPTION OF THE INVENTION

It has now been discovered that 1,3-dioxolane-4-carboxylic acid salts corresponding to the following general formula

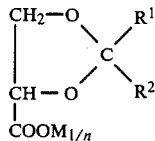

in which $R^1$ and $R^2$ are selected from the group consisting of a hydrogen atom and an alkyl group having 1–4 carbon atoms; M is selected from the group consisting of alkali metal ions, alkaline earth metal ions, ammonium ion, monoalkanolammonium ions containing 2–4 carbon atoms in the alkanol group, dialkanolammonium ions containing 2–4 carbon atoms in each alkanol group and trialkanolammonium ions containing 2–4 carbon atoms in each alkanol group; and n is the valency of M; may readily be produced by oxidizing with air or oxygen an isomer mixture of a 4-hydroxymethyl-1,3-dioxolane corresponding to the following general formula

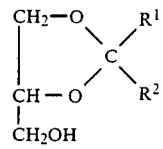

wherein $R^1$ and $R^2$ are as defined above, and a 5-hydroxy-1,3-dioxane in the presence of a platinum metal catalyst and a base at a pH in the range of about 7 to 14. The above isomer mixture is obtained from the reaction of glycerin with an aldehyde or ketone of the formula $R^1R^2CO$, wherein $R^1$ and $R^2$ are as defined above. The salts of formula I are produced by selectively oxidizing the dioxolane with oxygen or air in the presence of a platinum metal catalyst and a base at a pH in the range of about 7 to 14 and isolating the salt from the reaction mixture.

It has further been discovered that salts of 1,3-dioxolane-4-carboxylic acid have excellent moisture-binding properties and are well suited for use as humectants for technical purposes and especially as skin humectants in cosmetic preparations.

Under the oxidation conditions described hereinbelow, the 4-hydroxymethyl-1,3-dioxolane isomer is selectively oxidized, so that the 5-hydroxy-1,3-dioxane isomer corresponding to the following general formula

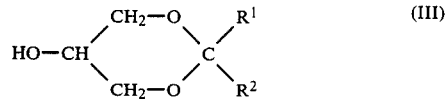

in which $R^1$ and $R^2$ are as defined above, can be readily isolated from the reaction mixture.

The process of the present invention is of particular value for the production of the 1,3-dioxolane-4-carboxylic acids of general formula (I) in which $R^1$ is hydrogen and $R^2$ is a $C_1$–$C_4$ alkyl group.

The oxidation reaction is carried out in an aqueous medium at a pH in the range of 7 to 14, i.e., in the alkaline range. Particularly suitable bases are, for example, sodium and potassium hydroxide, sodium and potassium carbonate, sodium and potassium hydrogen carbonate, calcium hydroxide and barium hydroxide. However, ammonia, mono-, di- and trialkanolamines containing from 2 to 4 C-atoms in each of the alkanol group(s), and preferably containing 2 to 3 C-atoms, are also suitable. The base is preferably added to the isomer mixture in a quantity of from about 1 to 1.5 moles per mole of 4-hydroxymethyl-1,3-dioxolane.

Palladium or platinum is preferably used as the catalyst from the group of metallic elements commonly known as platinum metals (cf. Hackh's Chemical Dictionary (1969), McGraw-Hill Book Co.) Other platinum metals include osmium, iridium, rhodium, ruthenium, technectium and rhenium. The catalyst is preferalby deposited on a solid support. Particularly high yields are obtained where an activated carbon treated with palladium is used as the catalyst.

The oxidizing agent used is preferably oxygen either in the form of pure oxygen or in the form of air. The oxidation reaction may be carried out at atmospheric pressure. However, a pressure higher than atmospheric pressure is preferably used. The reaction rate may be accelerated, particularly where air is used as the oxidizing agent, by conducting the reaction at a gauge pressure of up to about 100 bar. The oxidation temperature may be in the range from about 20° to 100° C. and is preferably in the range of about 50° to 100° C. The progress of the reaction may be monitored by titrating the reactants to determine the quantity of 1,3-dioxolane-4-carboxylic acid formed. Where air is used as the oxidizing agent and the oxidation reaction is carried out at a temperature in the range of about 50° to 100° C. and under atmospheric pressure, the reaction normally is completed after about 2 to 6 hours. Where pure oxygen or elevated pressure is used, the reaction time can be shortened to as little as about 1-2 hours. As will be recognized by those skilled in the art, the reaction can be carried out in either a batchwise or continuous fashion using known equipment.

On completion of the oxidation reaction, the catalyst is removed as required, for example by filtration or sedimentation, and the pH adjusted to 8-9 to ensure that any 1,3-dioxolane-4-carboxylic acid formed is converted to its corresponding salt. Preferably, the same base used to adjust the alkalinity of the aqueous reaction medium is used. The non-oxidized 5-hydroxy-1,3-dioxane is readily separated from the reaction mixture by extraction with a solvent in which the 5-hydroxy-1,3-dioxane is soluble, but in which the salt of the 1,3-dioxolane-4-carboxylic acid is insoluble. Suitable solvents include, for example, chlorinated hydrocarbons, such as methylene chloride, chloroform, carbon tetrachloride, perchloroethylene, liquid hydrocarbons and other water-insoluble liquid solvents in which the salts of the 1,3-dioxolane-4-carboxylic acid are insoluble.

It is particularly advantageous to carry out the extraction after removal of any water, for example by a distillation process, in order to form a substantially anhydrous residue. In that case, it is even possible to use water-soluble solvents, particularly liquid ethers such as, for example, dioxane, ethylene glycol dimethyl ether or methyl tertiary butyl ether for the extraction step. The salts of the 1,3-dioxolane-4-carboxylic acid obtained by extraction may be further purified by crystallization from lower alcohols (i.e., $C_1-C_6$ alcohols), such as methanol or ethanol for example.

The 5-hydroxy-1,3-dioxanes corresponding to general formula III may be isolated from the solvent extracts and purified by removal of the solvent and distillation. The 5-hydroxy-1,3-dioxanes themselves are suitable as solvents for polar organic substances.

The salts of the 1,3-dioxolane-4-carboxylic acids corresponding to general formula I show high moisture binding power. Accordingly, they are suitable for use as humectants both for technical and also for cosmetic purposes. The ability of these compounds to keep skin moist is particularly good. Accordingly, the present invention also relates to methods of using the salts of 1,3-dioxolane-4-carboxylic acids corresponding to general formula I as humectants, particularly as skin humectants in cosmetic preparations.

The cosmetic preparations may be aqueous, aqueous-alcoholic or alcoholic solutions, for example, skin care lotions, face lotions, hair lotions; deodorizing or antiperspiration preparations in liquid, stick or aeorsol form or emulsions such as, for example, skin creams, skin emulsions or liquid or solid personal hygiene preparations such as, for example, shampoos, liquid soaps and solid soaps based on fatty acid soaps or on synthetic surfactants and any other cosmetic preparations used for application to the skin.

The typical cosmetic preparations mentioned above need not be modified in any substantial way in order to incorporate humectants comprising the salts of 1,3-dioxolane-4-carboxylic acids since there is complete compatibility between these salts and known constituents of cosmetic preparations. However, the cosmetic preparations should preferably have a pH in the neutral or alkaline range because 1,3-dioxolanes have short shelf lives in acidic mediums. The quantity of salts of 1,3-dioxolane-4-carboxylic acids used in such cosmetic preparations will of course depend at least in part on the other components of the preparation. Generally, however, from about 1 to 20%, preferably from about 3 to 10%, and more preferably from about 4 to 5% by weight, based on the weight of the preparation, can be employed.

The following Examples illustrate the advantages of the present invention. Those skilled in the art will appreciate that these examples are merely illustrative of, but do not in any way limit, the scope of the present invention which is defined in the appended claims.

EXAMPLE 1

Production of 1,3-dioxolane-4-carboxylic acid, sodium salt 40 g (385 mmoles) of a glycerin formal mixture obtained by reacting gylcerin and paraformaldehyde (the mixture consisting of 25% by weight of 4-hydroxymethyl-1,3-dioxolane and 75% by weight of 5-hydroxy-1,3-dioxane) and 3.8 g (95 mmoles) of sodium hydroxide were dissolved in 360 ml of water. The solution was introduced into a 40 mm diameter vertical chromatography tube having a sintered glass base and a liquid heating jacket. The solution was heated to 70° C. After the addition of 4 g of an activated carbon containing 5% by weight of palladium, air was passed through the sintered glass base for 3 hours at 70° C. at a flow rate of 0.8 l/minute.

After filtration, the pH which had fallen to 6.5 was increased to 8.5 by the addition of sodium hydroxide solution and the water was distilled off under reduced pressure using a water jet vacuum. The remaining residue was thoroughly washed three times with 50 ml of ethylene glycol dimethyl ether. After drying, the residue was found to contain 11 g (82% of the theoretical) of 1,3-dioxolane-4-carboxylic acid, Na salt. After dissolution in and crystallization from methanol, the salt's melting point was determined to be in the range of 230° to 234° C.

After removal of the solvent by distillation and distillation of the residue, 27.1 g (90% of the theorectical) of pure 5-hydroxy-1,3-dioxolane (boiling point 192° C., refractive index $n^{20} = 1.4529$) were obtained from the ethylene glycol dimethyl ether extract.

EXAMPLE 2a

Production of 2,2-dimethyl-1,3-dioxolane-4-carboxylic acid, sodium salt 40.7 g (308 mmoles) of a glycerin ketal mixture obtained by reacting glycerin and acetone (the mixture containing 97.5% by weight of 2,2-dimethyl-4-hydroxymethyl-1,3-dioxolane) and 12.2 g (305 mmoles) of sodium hydroxide were dissolved in 336 ml of water. The solution was oxidized with air in the presence of 4 g of activated carbon containing 5% by weight of Palladium under the same conditions as described in Example 1.

After removal of the catalyst by filtration, the solution, which still had a pH of 9.5, was adjusted to pH 8.5 by the addition of sulfuric acid. The water in the solution was distilled off under reduced pressure using a water jet vacuum. The remaining residue was hot-extracted with methyl-tert-butyl ether, with 1.1 g of the product being dissolved. The crude residue was dissolved in methanol and the undissolved constituents were separated by filtration. The residue-methanol solution was evaporated to complete dryness leaving 45 g (92% of the theoretical, based on the reacted product) of pure sodium salt of 2,2-dimethyl-1,3-dioxolane-4-carboxylic acid as the residue. The crude product had a melting point of 243°–245° C. The melting point of the recrystallized residue was about 249°–251° C.

EXAMPLE 2b

Oxidation under pressure 40.7 g (308 mmoles) of a glycerin ketal mixture containing 97.5% by weight of 2,2-dimethyl-4-hydroxymethyl-1,3-dioxolane and 12.2 g (305 mmoles) of sodium hydroxide were dissolved in 366 ml of water. After transferring the mixture to a nickel shaker-type autoclave, the solution was heated to about 80° C. under a pressure of 25 bar in the presence of 4 g of an activated carbon containing 5% by weight of palladium with agitation for about 2 hours. The pressure in the autoclave rose briefly to 30 bar, subsequently fell back to 25 bar and, after another hour, increased to 63 bar. After 2 hours, the pressure remained constant at 53 bar. The autoclave was then vented. The pH of the solution was adjusted, the water in the solution was distilled off, and the remaining residue was hot extracted in the same manner as described in Example 2. The 2,2-dimethyl-1,3-dioxolane-4-carboxylic acid, Na salt was isolated in a yield of 86% of the theoretical. The melting point of the salt was 243°–246° C.

EXAMPLE 3

Production of 2-ethyl-2-methyl-1,3-dioxolane-4-carboxylic acid, sodium salt 45.2 g (310 mmoles) of crude 2-ethyl-2-methyl-4-hydroxymethyl-1,3-dioxolane obtained by reacting glycerin and methyl ethyl ketone were oxidized with air under the same conditions as described in Example 2. The oxidation was carried out in the presence of 4 g of an activated carbon containing 5% by weight of palladium. The pH of the solution was adjusted, the water in the solution distilled off, and the remaining residue was hot extracted in the same manner as described in Example 2. The 2-ethyl-2-methyl-1,3-dioxolane-4-carboxylic acid, sodium salt was obtained in a yield of 85% of the theoretical. The melting point of the salt was 273°–276° C.

EXAMPLE 4

Measurement of moisture binding power and determination of the equilibrium moisture of 1,3-dioxolane-4-carboxylic acids 10 ml of sulfuric acid of the following concentrations were each introduced into one of six Erlenmeyer flasks:
0% by weight $H_2SO_4$ to adjust 100% rel. air humidity
19% by weight $H_2SO_4$ to adjust 89% rel. air humidity
36% by weight $H_2SO_4$ to adjust 65% rel. air humidity
45% by weight $H_2SO_4$ to adjust 47% rel. air humidity
53% by weight $H_2SO_4$ to adjust 30% rel. air humidity
80% by weight $H_2SO_4$ to adjust 1% rel. air humidity The flasks were tightly closed using glass stoppers and then stored for 24 hours at 25° C. in order to acquire a constant air humidity.

The glass stoppers were then replaced by others carrying a fused-on sample vessel into which an exactly weighed quantity, the quantity being within the range of 300–500 mg, of the test substance moistened with 100 mg of water was placed.

After storage for an additional 24 hours at 25° C. in a thermostat, the samples were reweighed. The amount of water taken up or given off at the particular air humidity was determined from the weight difference of each sample. Graphic interpolation was used to determine the relative air humidity at which the sample neither gave off nor took up water under the selected test conditions. This relative air humidity (r.H.) corresponds to the equilibrium moisture.

| Compound: | Equilibrium moisture: |
|---|---|
| 1,3-dioxolane-4-carboxylic acid, Na salt | 55% r.H. |
| 2,2-dimethyl-1,3-dioxolane-4-carboxylic acid, Na salt | 55% r.H. |
| 2,2-dimethyl-1,3-dioxolane-4-carboxylic acid, K salt | 45% r.H. |
| 2-ethyl-2-methyl-1,3-dioxolane-4-carboxylic acid, Na salt | 62% r.H. |

EXAMPLE 5

A moisturizing cream was prepared having the following composition:

| | |
|---|---|
| A self-emulsifying mixture of mono- and di- glycerides of higher saturated fatty acids, mainly palmitic and stearic acid, with potassium stearate sold by Dehydag Deutsche Hydrierwerke GmbH, Duesseldorf, Germany, under the Trademark CUTINA ® KD16 | 16% by weight |
| An adduct of 30 moles of ethylene oxide with cetyl stearyl alcohol sold by Henkel KGaA, Duesseldorf-Holthausen, Germany, under the Trademark EUMULGIN ® B3 | 1% by weight |
| 2-octyl dodecanol | 12% by weight |
| Isopropyl myristate | 8% by weight |
| Paraffin oil (viscous liquid) | 4% by weight |
| 2,2-dimethyl-1,3-dioxolane-4-carboxylic acid, Na salt | 5% by weight |
| Sorbitol solution (70% in water) | 8% by weight |
| p-hydroxybenzoic acid methyl ester | 0.2% by weight |
| Water | 45.8% by weight |

EXAMPLE 6

A hair lotion was prepared having the following composition:

| | |
|---|---|
| Ethanol | 49.1% by weight |
| Hamamelis extract | 5.0% by weight |
| Peru balsam | 0.8% by weight |
| 2,2-dimethyl-1,3-dioxolane-4-carboxylic acid, Na salt | 4.0% by weight |
| Perfume oil | 0.2% by weight |
| Water | 40.9% by weight |

I claim:

1. A process for producing a 1,3-dioxolane-4-carboxylic acid salt having the general formula (I):

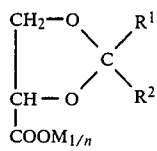

in which:

R¹ is hydrogen and R² is hydrogen or an alkyl group having 1-4 carbon atoms;

M is selected from the group consisting of alkali metal ions, alkaline earth metal ions, ammonium ion, monoalkanolammonium ions containing 2-4 carbon atoms in the alkanol group, dialkanolammonium ions containing 2-4 carbon atoms in each of the alkanol groups, and trialkanolammonium ions containing 2-4 carbon atoms in each of the alkanol groups; and n is the valency of M comprising:

(a) reacting glycerin with an aldehyde having a general formula R¹R²CO, in which R¹ and R² are as defined above to form an isomer mixture of 4-hydroxymethyl-1,3-dioxolane having the general formula

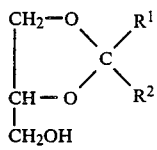

wherein R¹ and R² are as defined above, and a 5-hydroxy1,3-dioxane;

(b) selectively oxidizing with air or oxygen the 4-hydroxymethyl-1,3-dioxolane in the isomer mixture in the presence of a catalyst seslected from the platinum metals group and a base in an aqueous reaction medium at a pH in the range or about 7 to 14; and (c) isolating the 1,3-dioxolane-4-carboxylic acid salt from the reaction medium.

2. A process as defined in claim 1, wherein R² is an alkyl group containing 1-4 carbon atoms.

3. A process as defined in claim 1, wherein the base is selected from the group consisting of sodium hydroxide, potassium hydroxide, sodium carbonate, potassium carbonate, sodium hydrogen carbonate, potassium hydrogen carbonate, calcium hydroxide and barium hydroxide.

4. A process as defined in claim 1, wherein the oxidizing is carried out with oxygen under a pressure of from 1 to 100 bar and at a temperature of 50° to 100° C.

5. A process as defined in claim 1, wherein the acid salt is isolated from the aqueous reaction medium by removing 5-hydroxy-1,3-dioxane from the medium by extraction with a solvent.

6. The process of claim 1, wherein the acid salt is isolated by selectively dissolving and extracting the 5-hydroxy-1,3-dioxane in a solvent, the acid salt being insoluble in the solvent.

7. The process as defined in claim 1 wherein the catalyst comprises palladium on an activated carbon support.

8. The process as defined in claim 1, wherein the isolating of the acid salt from the reaction medium comprises distilling water from the medium yielding an anhydrous residue and selectively extracting the 5-hydroxy-1,3-dioxane with a solvent, the acid being insoluble in the solvent.

* * * * *